US012698536B2

(12) United States Patent
Fujii

(10) Patent No.:  US 12,698,536 B2
(45) Date of Patent:  Aug. 4, 2026

(54) ROTAVIRUS GENOTYPE DETECTION METHOD AND GENE AMPLIFICATION PRIMER SET USED IN SAME

(71) Applicants: SHIMADZU CORPORATION, Kyoto (JP); Japan Institute for Health Security, Tokyo (JP)

(72) Inventor: Yoshiki Fujii, Tokyo (JP)

(73) Assignees: SHIMADZU CORPORATION, Kyoto (JP); JAPAN INSTITUTE FOR HEALTH SECURITY, Tokyo (JP)

( * ) Notice: Subject to any disclaimer, the term of this patent is extended or adjusted under 35 U.S.C. 154(b) by 1314 days.

(21) Appl. No.: 17/277,069

(22) PCT Filed: Oct. 2, 2019

(86) PCT No.: PCT/JP2019/038893
§ 371 (c)(1),
(2) Date: Oct. 21, 2021

(87) PCT Pub. No.: WO2020/071419
PCT Pub. Date: Apr. 9, 2020

(65) Prior Publication Data
US 2022/0042115 A1     Feb. 10, 2022

(30) Foreign Application Priority Data
Oct. 3, 2018     (JP) ................................. 2018-188665

(51) Int. Cl.
*C12Q 1/6888*     (2018.01)
*C12Q 1/686*     (2018.01)
(52) U.S. Cl.
CPC ........... *C12Q 1/6888* (2013.01); *C12Q 1/686* (2013.01)
(58) Field of Classification Search
CPC .................................................. C12Q 1/6888
See application file for complete search history.

(56) References Cited

U.S. PATENT DOCUMENTS

2009/0170066 A1     7/2009   Colau et al.
2009/0246829 A1*   10/2009   Buonagurio ........... C12Q 1/701
                                                                        435/254.2
2013/0267429 A1*   10/2013   Gardner ................ C12Q 1/6876
                                                                        506/8

FOREIGN PATENT DOCUMENTS

WO     WO-2014197607 A1 * 12/2014   ......... G01N 33/5308

OTHER PUBLICATIONS

Simple Cloning Lab: Hybridisation ; www.bioinformatics.nl; Archived Aug. 10, 2017 on WaybackMachine (Year: 2017).*

Wikipedia—Gene: web.archive.org/web/20180917044235/https://en.wikipedia.org/wiki/Gene; Archived Sep. 17, 2018 on WaybackMachine (Year: 2018).*
Fujii et al. Improvement of Rotavirus Genotyping Method by Using the Semi-Nested Multiplex-PCR With New Primer Set. Front Microbiol. Mar. 29, 2019;10:647. doi: 10.3389/fmicb.2019.00647. PMID: 30984154; PMCID: PMC6449864 (Year: 2019).*
Wikipedia: web.archive.org/web/20180917044235/https://en.wikipedia.org/wiki/Gene; Archived Sep. 17, 2018 on WaybackMachine (Year: 2018).*
Office Action issued May 10, 2022 in corresponding Japanese Patent Application No. 2020-550495.
Office Action issued Oct. 25, 2022 in corresponding Japanese Patent Application No. 2020-550495, with machine English language translation.
Office Action issued Sep. 24, 2024 in corresponding Japanese Patent Application No. 2020-550495, with machine English-language translation.
Iturriza-Gomara et al., "Rotavirus genotyping: keeping up with an evolving, population of human rotayiruses", Journal of Clinical Virology, vol. 31, 2004, pp. 259-265.
Cowley et al., "Emergence of a novel equine-like G3P[8] intergenogroup reassortant rotavirus strain associated with gastroenteritis in Australian children" Journal of General Virology, 2016, vol. 97, pp. 403-410.
Fujii et al., "Improvement of Rotavirus Genotyping Method by Using the Semi_Nested Multiplex-PCR with New Primer Set", Frontiers in Microbiology, vol. 10, Article 647, Mar. 2019, pp. 1-6.
Lambert et al., "Early evidence for direct and indirect effects of the infant rotavirus vaccine program in Queensland", MJA, Aug. 2009, vol. 191, No. 3, pp. 157-160.
Leshem et al., "Rotavirus Vaccines and Health Care Utilization for Diarrhea in the United States (2007-2011)", Pediatrics, vol. 134, No. 1, Jul. 2014, pp. 15-23.
Karafillakis et al., "Effectiveness and impact of rotavirus vaccines in Europe, 2006-2014", Vaccine, vol. 33, 2015, pp. 2097-2107.
Fujii et al., "Effectiveness of rotavirus vaccines against hospitalisations in Japan", BMC Pediatrics, 2017, vol. 17, No. 156, pp. 1-7.

(Continued)

*Primary Examiner* — Aaron A Priest
*Assistant Examiner* — Tian Nmn Yu
(74) *Attorney, Agent, or Firm* — Wenderoth, Lind & Ponack, L.L.P.

(57)     ABSTRACT

The present invention addresses the problem of finding a new gene detection primer capable of more accurately detecting genotypes of rotavirus A and a detection means using the gene detection primer, and provides a rotavirus genotype detection method, a gene amplification primer set used in this method, and a genotype detection kit. In the rotavirus genotype detection method, (A) using a base sequence at positions from 174 to 834 of a VP7 gene segment of a G1 type strain of the rotavirus A as a base sequence counting reference, sense primers each aligned to one to four kinds of base sequence regions selected from (1) the positions from 802 to 834 (corresponding to G3 type), (2) the positions from 747 to 789 (corresponding to equine-like G3 type), (3) the positions from 603 to 636 (corresponding to G9 type), and (4) the positions from 666 to 711 (corresponding to G12 type) are used as basic gene amplification sense primers, and (B) using the above positions from 883 to 1062 as the counting reference, antisense primers each aligned to a region of the base sequence of the counting reference are used as gene amplification common antisense primers.

3 Claims, 2 Drawing Sheets

Specification includes a Sequence Listing.

(56)  References Cited

OTHER PUBLICATIONS

Gouvea et al., "Polymerase Chain Reaction Amplification and Typing of Rotavirus Nucleic Acid from Stool Specimens", Journal of Clinical Microbiology, Feb. 1990, vol. 28, No. 2, pp. 276-282.

Mitui et al., "Inaccurate identification of rotavirus genotype G9 as genotype G3 strains due to primer mismatch", Virology Journal, 2012, vol. 9, No. 144, pp. 1-5.

Written Opinion of International Searching Authority issued Dec. 24, 2019 in International (PCT) Application No. PCT/JP2019/038893, with partial English translation.

International Search Report issued Dec. 24, 2019 in International (PCT) Application No. PCT/JP2019/038893.

* cited by examiner

ROTAVIRUS GENOTYPE DETECTION METHOD AND GENE AMPLIFICATION PRIMER SET USED IN SAME

TECHNICAL FIELD

The present invention relates to a virus genotype detection means, more specifically, a genotype detection method of a rotavirus, in particular, rotavirus A, a gene amplification primer set used in this method, and a genotype detection kit including the primer set.

BACKGROUND ART

A rotavirus is a virus that causes acute gastroenteritis in various mammals and birds and belongs to the Reoviridae family. Further, the rotavirus is classified into nine groups (A to I) which do not show serologic cross-reactivity of the inner capsid protein VP6. Among these rotaviruses, rotavirus A (RVA) belongs to the most frequently detected group.

Worldwide, RVA is a major cause of gastroenteritis among babies. RVA caused 128,500 deaths among children younger than 5 years globally in 2016 (Troeger JAMA Pediatr. 2018 Aug. 13. doi: 10.1001/jamapediatrics. 2018. 1960). RVA also imposes a substantial burden in developed countries including Japan (Nakagomi et al., Jpn J Infect Dis 2013, 66 (4), 269-275).

RVA, viruses abundantly found in the feces of patients, is clinically diagnosed at a sufficient level by a simple testing kit using an immunochromatography method. However, genotype diagnosis is required for conducting molecular epidemiology studies and investigating changes in genotypic trends after vaccination and the like.

Two attenuated live RVA vaccines have already been introduced in Japan (Rotarix: November 2011 and RotaTeq: July 2012). Although the RVA vaccines are effective (Non Patent Documents 1 to 4), selection pressure of the vaccines may cause a shift of the epidemic strains. Thus, it becomes increasingly important to conduct investigation and surveillance of changes in genotypic distribution of RVA.

PRIOR ART DOCUMENTS

Non-Patent Documents

Non-Patent Document 1: Lambert et al., Med J Aust 2009, 191(3), 157-160.
Non-Patent Document 2: Leshem et al., Pediatrics 2014, 134(1), 15-23.
Non-Patent Document 3: Karafillakis et al., Vaccine 2015, 33(18), 2097-2107.
Non-Patent Document 4: Fujii et al., BMC Pediatr 2017, 17(1), 156.
Non-Patent Document 5: Gouvea et al., J Clin Microbiol 1990, 28(2), 276-282.
Non-Patent Document 6: Mitui et al., Virol J 2012, 9, 144

SUMMARY OF THE INVENTION

Problems to be Solved by the Invention

As a means for conducting surveillance of the genotypic distribution of rotavirus A (RVA), a genotype detection method in which a gene amplification product obtained by a gene amplification method such a PCR method is analyzed is used. In particular, there is used a nested PCR method in which an RVA gene amplification product in a specimen is first obtained by RT-PCR in a first step and then PCR in a second step is further performed using an RVA genotype specific primer to amplify an RVA genotype specific gene. As a gene amplification primer used in this PCR in the second step, a VP7 primer set reported by Gouvea et al. in 1990 is used worldwide up to now (Non Patent Document 5). However, since the primer sequence remains largely unimproved up to the present, it has been reported that some genotypes of RVA strains are erroneously determined using this primer set (Mitui et al., Virol J 2012, 9, 144). As described above, RVA vaccination causes a gradual shift of the epidemic strains, making it necessary to provide a new gene detection primer capable of detecting the genotype of RVA more accurately.

Means for Solving the Problems

As a result of conducting studies for solving the above problems, the present inventors have found, in genotype detection of RVA using a gene amplification method such a PCR method, an RVA gene small region which allows designing of a gene amplification primer having high specificity to each genotype of RVA, that is, capable of accurately detecting the genotype of RVA in a sample without causing a cross-reaction to the genotypes other than the desired genotype or without causing erroneous determination, in conjunction with the corresponding RVA genotype, thereby successfully providing an RVA genotype detection method using the gene amplification primer and a primer set for detecting the gene.

The present invention includes (1) an RVA genotype detection method (also referred to as a detection method of the present invention), (2) a gene amplification primer set used for the detection method (also referred to as a primer set of the present invention), and (3) an RVA genotype detection kit including the primer set (also referred to as a kit of the present invention).

<Detection Method of Present Invention>

The detection method of the present invention is a method for detecting a genotype of a rotavirus using the following "sense primers (A)" and "common antisense primers (B)". The Sense Primers (A) are (A) using a base sequence of a positive strand at positions from 174 to 834 in the base sequence of double stranded RNA or its complementary DNA of a VP7 gene segment (a segment 9) of a G1 type strain (Wa strain) of rotavirus A as a base sequence counting reference:

(1) one or more kinds of the sense primers hybridizing to a negative strand toward the base sequence at the positions from 802 to 834 (the positive strand number) of the double-stranded RNA or its complementary DNA of the VP7 gene segment of a G3 (a human rotavirus) type strain (AU-1) of the rotavirus A;

(2) one or more kinds of the sense primers hybridizing to the negative strand toward the base sequence at the positions from 747 to 789 (the positive strand number) of the double-stranded RNA or its complementary DNA of the VP7 gene segment of an equine-like G3 (an equine-like rotavirus) type strain (S13-30) of the rotavirus A;

(3) one or more kinds of the sense primers hybridizing to the negative strand toward the base sequence at the positions from 603 to 636 (the positive strand number) of the double-stranded RNA or its complementary DNA of the VP7 gene segment of a G9 type strain (B3458) of the rotavirus A; and (4) one or more kinds of the sense primers hybridizing to the negative strand toward the base sequence at the positions from 666 to 711 (the positive strand number) in the base sequence of the double-stranded RNA or its complementary DNA of the VP7 gene segment of a G12 type strain (Dhaka25) of the rotavirus A, and the common antisense primers (B) are (B) using the base sequence of the positive strand at the positions from 883 to 1062 of the G1 type strain as the counting reference, one or more kinds selected from common antisense primers hybridizing to the positive strands of the rotavirus A type strains described in the (1) to (4), each of the positive strands being aligned to a region of the base sequence used as the counting reference.

A detection method of the present invention is a detection method for detecting a genotype of a rotavirus by using a gene amplification product obtained by applying a gene amplification means to a gene obtained from a specimen, in which the gene amplification means uses gene amplification primers including sense primers (A) and common antisense primers (B).

In the detection method of the present invention, in addition to the abovementioned (1) to (4), the sense primers (A) are used by further including one to four kinds selected from the following (5) to (8)(hereinafter, these are also referred to as "additional sense primers):

(5) one or more kinds of the sense primers hybridizing to the negative strand toward the base sequence at the positions from 297 to 338 (the positive strand number) of the double-stranded RNA or its complementary DNA of the VP7 gene segment of the G1 type strain (Wa strain) of the rotavirus A;

(6) one or more kinds of the sense primers hybridizing to the negative strand toward the base sequence at the positions from 399 to 438 (the positive strand number) of the double-stranded RNA or its complementary DNA of the VP7 gene segment of a G2 type strain (KUN) of the rotavirus A;

(7) one or more kinds of the sense primers hybridizing to the negative strand toward the base sequence at the positions from 468 to 507 (the positive strand number) of the double stranded RNA or its complementary DNA of the VP7 gene segment of a G4 type strain (BrB-9) of the rotavirus A; and (8) one or more kinds of the sense primers hybridizing to the negative strand toward the base sequence at the positions from 174 to 210 (the positive strand number) of the double-stranded RNA or its complementary DNA of the VP7 gene segment of a G8 type strain (NP-130) of the rotavirus A.

A G1 type strain of RVA is defined by the above "Wa strain". The term "Wa strain" represents a strain name of the RVA VP7 gene of this strain. The RVA type strains with other genotypes are also disclosed in the same format in the preset specification.

The term "base sequence counting reference" refers to reference on the basis of which the number of the base sequence is counted in the RVA type strains including the ones with other genotypes. The base sequences of the RVA type strains other than the G1 type selected as detection targets are specified in a state of being aligned to the base sequence of the VP7 gene of the G1 type strain. In a case where there is a base deletion or insertion compared to the base sequence of the VP7 gene of the G1 type strain, the base sequence number is counted by including those events. For example, in a G9 type strain (B3458) of RVA, a base corresponding to the base of the G1 type at position 1028 is deleted. Thus, a base sequence region of the G9 type corresponding to the base sequence region of the G1 type at the positions from 883 to 1062 is specified as the positions from 883 to 1061 according to the base sequence alignment. In this case, the bases in the region of the G9 type at the positions from 883 to 1027 are aligned as it is to the bases of the G1 type at the positions from 883 to 1027. However, the base (deletion) of the G9 type corresponding to the base of the G1 type at the position 1028 is skipped, and the base of the G9 type at the position 1028 is aligned to the base of the G1 type at the position 1029, and, thereafter, the bases of the G9 type at the positions from 1028 to 1061 are aligned to the bases of the G1 type at the positions from 1029 to 1062. Note that the "base sequence counting reference" provides a relative counting method, thus it is possible to use the type strains other than G1 type as the counting reference strain. In such a case, the present invention remains substantially unchanged.

Hybridization to double-stranded RNA or its complementary DNA of a specific type strain refers to a phenomenon in which a primer of interest hybridizes to target nucleotides serving as a template so as to function as a gene amplification primer in a gene amplification method such as a PCR method. This naturally includes a case of being completely complementary, but also a case where about 15% or less of the bases are not complementary (e.g., 3 bases or less in a case of a gene amplification primer having 20 bases in length). The target nucleotides include RNA since the target nucleotides serving as an initial template are the double stranded RNA of RVA in any gene amplification method to be used. For example, in a case of using a gene amplification means based on a PCR method, an initial gene amplification means is an RT-PCR method.

Further, a hybridization region of the gene amplification primer may be the entire or a part of the primer. For example, a modification such as a tag sequence suitable for the selected gene amplification means may be applied to the gene amplification primer.

The sense primers corresponding to the genotypes of the RVA type strains in the above 8 base sequence regions are defined by the sense primers (A) including the additional sense primers. Each of such sense primers may include one or more kinds of primers, and two or more kinds of the sense primers may be used in the same corresponding region. For example, a plurality of kinds of the sense primers, corresponding to the same type strain, in which a specific base is diversified (e.g., a specific base is set to A or G), may be used as mixed primers in the same corresponding base sequence region.

The term "gene amplification means" used in the detection method of the present invention is not limited, and examples thereof include a PCR method, an NASBA method, a LAMP method, an LCR method, and methods based on these gene amplification methods. The "gene amplification means" of the present invention is not limited to the gene amplification methods currently available, but also includes a gene amplification method that will be provided in the future as long as it is applicable to the present invention. The detection method of the present invention can be performed under specific conditions according to the individual gene amplification means applied to the present invention.

In the present invention, the gene amplification means based on the PCR method is one of modes preferably used. As specific examples thereof, a PCR method and an RT-PCR method can be used, and, further, a nested PCR method and a semi-nested PCR method can be preferably used, without being limited thereto. Further, the detection method of the present invention can also detect the genotypes of RVA with high sensitivity by performing a multiplex PCR method in which two or more kinds of the sense primers (A) potentially including the additional sense primers corresponding to a plurality of the genotypes of RVA, each primer being highly specific to the corresponding genotype of RVA, and the common antisense primers (B) are used together to make a reaction in a thermal cycler.

In general, using more kinds of the gene amplification primers in the multiplex PCR method makes it harder to accurately detect the genotypes as the risk of causing erroneous determination synergistically increases. The gene amplification primers used in the detection method of the present invention are highly specific to the corresponding genotypes of RVA, thus, even when the multiplex PCR method is performed by using the sense primers corresponding to a plurality of, for example, 3 to 8 different genotypes of RVA, the risk of causing erroneous determination can be minimized. In particular, the detection method of the present invention can be preferably performed when the sense primers (A) potentially including the additional sense primers are used as nested sense primers and the common antisense primers (B) are used as common nested antisense primers in a second amplification step in the nested PCR method (including the semi-nested PCR method).

In a case where the gene amplification method is directly applied to the RVA gene (double-stranded RNA) without using the nested PCR method (including the semi-nested PCR method) as the gene amplification method, the detection method of the present invention can be performed by carrying out the RT-PCR method in which the above set of the "sense primers (A) potentially including the additional sense primers" and the "common antisense primers (B)" are used.

Further specific description is given of a case where the nested PCR method (including the semi-nested PCR method) is used as the gene amplification method. In this case, the above set of the "sense primers (A) potentially including the additional sense primers" and the "common antisense primers (B)" is used in the second amplification step in the nested PCR method (including the semi-nested PCR method). In this step, as described above, the sense primers (A) are used as the nested sense primers while the common antisense primers (B) are used as the common nested antisense primers.

Then, in a first amplification step of the RT-PCR method, a gene amplification product of the first amplification step is obtained by using, as the gene amplification primers, (1) using the base sequence of the positive strand at the positions from 1 to 72 in the base sequence of the double-stranded RNA or its complementary DNA of a VP7 gene segment (a segment 9) of the G1 type strain (Wa strain) of rotavirus A as the base sequence counting reference, common outer sense primers hybridizing to the negative strands corresponding to the base sequences of positive strands of the type strains of rotavirus A having the different genotypes as detection targets, each of the base sequences of the positive strands being aligned to the entire or a part of the base sequence used as the base sequence counting reference, and (2) using the base sequence of the positive strand at the positions from 883 to 1062 of the above G1 type strain is used as the base sequence counting reference, common outer antisense primers hybridizing to the base sequences of the positive strands of the type strains of rotavirus A having the different genotypes as the detection targets, the base sequences of the positive strands being aligned to the entire or a part of the base sequence used as the base sequence counting reference. The gene amplification product is then used as templates in the above second amplification step, so that the nested PCR method (including the semi-nested PCR method) can be applied to the detection method of the present invention.

In the detection method of the present invention, the kinds of the RVA type strains to be selected for confirming hybridization are not particularly limited. Examples thereof include a G3 (a human rotavirus) type strain (AU-1), an equine-like G3 (an equine-like rotavirus) type strain (S13-30), a G9 type strain (B3458), and a G12 type strain (Dhaka25). Examples thereof further include the G1 type strain (Wa strain), a G2 type strain (KUN), a G4 type strain (BrB-9), and a G8 type strain (NP-130).

Of these, in a preferable basic embodiment of the detection method of the present invention, at least "the G3 type (the human rotavirus), the equine-like G3 type (the equine-like rotavirus), the G9 type, and the G12 type", in a further narrowed list, "the G3 type (the human rotavirus), the equine-like G3 type (the equine-like rotavirus), and the G9 type" are included as a basis for selecting the type strains of RVA as the detection targets. Further, in another preferable embodiment, "the G1 type, the G2 type, the G4 type, and the G8 type", in a further narrowed list, "the G1 type, the G2 type, and the G8 type" are added to the above list for selecting the type strains of RVA. From the viewpoint of detecting the genotypes of RVA as widely and efficiently as possible, in yet another preferable embodiment, all of the genotypes of the type strains, "the G3 type (the human rotavirus), the equine-like G3 type (the equine-like rotavirus), the G9 type, the G12 type, the G1 type, the G2 type, the G4 type, and the G8 type", are selected as disclosed in Example.

The RVA type strains in which common hybridization needs to be confirmed for creating the common antisense primers are the same as the type strains selected for the above sense primers.

All of the gene amplification primers described above have preferably 10 to 40 bases in length, more preferably 15 to 30 bases in length, in a case where the gene amplification means is based on the PCR method. In a case where the gene amplification methods other than the PCR method are used, the base length of the gene amplification primers may be appropriately selected according to other gene amplification methods.

Specimens applied to the detection method of the present invention include, for example, a sample separated from a living body in which the rotavirus may be present and a medium for research containing viruses amplified and maintained by culture cells or the like. Specific examples of the specimens include samples from feces, vomit, the blood, the marrow fluid, breast milk, a medium for research, and environment (food, tableware, clothes, a diaper, sewage, river water, etc.). All of these samples are separated from the living bodies.

<Primer Set of Present Invention>

The primer set of the present invention is a gene amplification primer set for performing the above detection method of the present invention. Specifically, it is provided as the following modes. Each mode can be used as the gene amplification primers used in the above detection method of the present invention.

(I)-1: Basic Sense Primer Set

A basic sense primer set is a gene amplification primer set for a purpose of detecting the genotype of the rotavirus, including one to four kinds of the sense primers selected from the following (1) to (4):

using a base sequence of a positive strand at positions from 174 to 834 in the base sequence of double-stranded RNA or its complementary DNA of a VP7 gene segment (a segment 9) of a G1 type strain (Wa strain) of rotavirus A as a base sequence counting reference:

(A)(1) one or more kinds of the sense primers hybridizing to a negative strand toward the base sequence at the positions from 802 to 834 (the positive strand number) of the double-stranded RNA or its complementary DNA of the VP7 gene segment of a G3 (a human rotavirus) type strain (AU-1) of the rotavirus A;

(A)(2) one or more kinds of the sense primers hybridizing to the negative strand toward the base sequence at the positions from 747 to 789 (the positive strand number) of the double-stranded RNA or its complementary DNA of the VP7 gene segment of an equine-like G3 (an equine-like rotavirus) type strain (S13-30) of the rotavirus A;

(A)(3) one or more kinds of the sense primers hybridizing to the negative strand toward the base sequence at the positions from 603 to 636 (the positive strand number) of the double-stranded RNA or its complementary DNA of the VP7 gene segment of a G9 type strain (B3458) of the rotavirus A; and (A)(4) one or more kinds of the sense primers hybridizing to the negative strand toward the base sequence at the positions from 666 to 711 (the positive strand number) in the base sequence of the double-stranded RNA or its complementary DNA of the VP7 gene segment of the G12 type strain (Dhaka25) of the rotavirus A.

(I)-2: Sense primer set potentially including additional sense primers

In this gene amplification primer set, one to four kinds of the sense primers selected from the following (A)(5) to (8)(additional sense primers) are further added to the above basic sense primer set.

(A)(5) one or more kinds of the sense primers hybridizing to the negative strand toward the base sequence at the positions from 297 to 338 (the positive strand number) of the double-stranded RNA or its complementary DNA of the VP7 gene segment of the G1 type strain (Wa strain) of the rotavirus A;

(A)(6) one or more kinds of the sense primers hybridizing to the negative strand toward the base sequence at the positions from 399 to 438 (the positive strand number) of the double-stranded RNA or its complementary DNA of the VP7 gene segment of a G2 type strain (KUN) of the rotavirus A;

(A)(7) one or more kinds of the sense primers hybridizing to the negative strand toward the base sequence at the positions from 468 to 507 (the positive strand number) of the double-stranded RNA or its complementary DNA of the VP7 gene segment of a G4 type strain (BrB-9) of the rotavirus A; and (A)(8) one or more kinds of the sense primers hybridizing to the negative strand toward the base sequence at the positions from 174 to 210 (the positive strand number) of the double-stranded RNA or its complementary DNA of the VP7 gene segment of a G8 type strain (NP-130) of the rotavirus A.

The sense primers corresponding to the genotypes of the RVA type strains in the above 8 base sequence regions are defined by the above sense primers (A) including the additional sense primers. Each of such sense primers may include one or more kinds of primers, and two or more kinds of the sense primers may be used in the same corresponding region as a configuration of the sense primer set. For example, a plurality of kinds of the sense primers, corresponding to the same type strain, in which a specific base is diversified (e.g., a specific base is set to A or G), may be chosen as mixed primers in the same corresponding base sequence region and used as the sense primer set.

Of those mentioned above, in a preferable basic embodiment as the sense primer set, at least "the G3 type (the human rotavirus), the equine-like G3 type (the equine-like rotavirus), the G9 type, and the G12 type", in a further narrowed list, "the G3 type (the human rotavirus), the equine-like G3 type (the equine-like rotavirus), and the G9 type" are included as a basis for selecting the type strains of RVA as the detection targets. Further, in another preferable sense primer set, "the G1 type, the G2 type, the G4 type, and the G8 type", in a further narrowed list, "the G1 type, the G2 type, and the G8 type" are added to the above list for selecting the type strains of RVA. From the viewpoint of detecting the genotypes of RVA as widely and efficiently as possible, in yet another preferable sense primer set, all of the genotypes of the type strains, "the G3 type (the human rotavirus), the equine-like G3 type (the equine-like rotavirus), the G9 type, the G12 type, the G1 type, the G2 type, the G4 type, and the G8 type", are applicable as disclosed in Example.

The above sense primer sets (I)-1 and (I)-2 can be combined with appropriate antisense primers and used to perform the detection method of the present.

(II) Set of Sense Primers and Antisense Primers

In this primer set, the "basic sense primer set" in (I)-1 or the "sense primer set potentially including the additional sense primers" in (I)-2 described above are combined with the antisense primers (B).

Specifically, in addition to the sense primers in (I)-1 or (I)-2 mentioned above, the gene amplification primer set includes in combination with, using the base sequence of the positive strand at the positions from 883 to 1062 in the base sequence of the double-stranded RNA or its complementary DNA of the VP7 gene segment (the segment 9) of the G1 type strain (Wa strain) of the rotavirus A as the counting reference, one or more kinds of the common antisense primers (B) hybridizing to the positive strands of the type strains of the rotavirus A, each of the positive strands being aligned to a region of the base sequence used as the counting reference.

The above set (II) of the sense primers and the antisense primers can be used to perform the detection method of the present invention.

(III) Primer Set Used for Performing Nested PCR Method.

This primer set is used when the nested PCR method is performed as the RVA genotype detection means.

Specifically, the gene amplification primer set according to (I)-1, (I)-2, or (II) described above, in which the gene amplification primer set is included as the primer set used in the second amplification step of the nested PCR method, and (1) using the base sequence of the positive strand at the positions from 1 to 72 in the base sequence of the double-stranded RNA or its complementary DNA of the VP7 gene segment (the segment 9) of the G1 type strain (Wa strain) of the rotavirus A as the base sequence counting reference, the common outer sense primers hybridizing to the negative strands corresponding to the base sequences of the positive strands of the type strains the rotavirus A having the different genotypes as the detection targets, each of the base sequences of the positive strands being aligned to the entire or a part of the base sequence used as the base sequence counting reference, and (2) using the base sequence of the positive strand at the positions from 883 to 1062 of the G1 type strain as the base sequence counting reference, the common outer antisense primers hybridizing to the base sequences of the positive strands of the type strains of the rotavirus A having the different genotypes as the detection targets, the base sequences of the positive strands being aligned to the entire or a part of the base sequence used as the base sequence counting reference, are included as the primer set used in the first amplification step of the nested PCR method using the RT-PCR method.

The above primer set (III) of the present invention can be used for performing the detection method of the present invention by using the nested PCR method.

All of the gene amplification primers in the primer set of the present invention according to (I)-1, (I)-2, (ii), or (III) described above have preferably 10 to 40 bases in length, more preferably 15 to 30 bases in length, in a case where the gene amplification means is based on the PCR method. In a case where the gene amplification methods other than the PCR method are used, the base length of the gene amplification primers may be appropriately selected according to other gene amplification methods.

<Kit of Present Invention>

A kit of the present invention is a detection kit including the primer set of the present invention as a constituent element in order to perform the detection method of the present invention using the primer set of the present invention. The kit of the present invention can include other constituent elements in accordance with specific modes of the detection method of the present invention. Specifically, for example, in a case where the gene amplification means is a method based on the PCR method, a PCR enzyme (DNA polymerase), reverse transcriptase, a buffer solution, a metal ion functioning as an enzyme cofactor (a magnesium ion, etc.), deoxyribonucleoside triphosphates as substrates of DNA amplification (dNTP (mixture of dATP, dCTP, dGTP, and TTP)), water for dilution, and the like can be included as other constituent elements.

Effects of the Invention

According to the present invention, a means for accurately detecting the genotypes of RVA (rotavirus A) on the basis of the gene amplification method such as the PCR method can be provided as the detection method, the gene amplification primer set, and the detection kit.

MODE FOR CARRYING OUT THE INVENTION

Figure 1A:
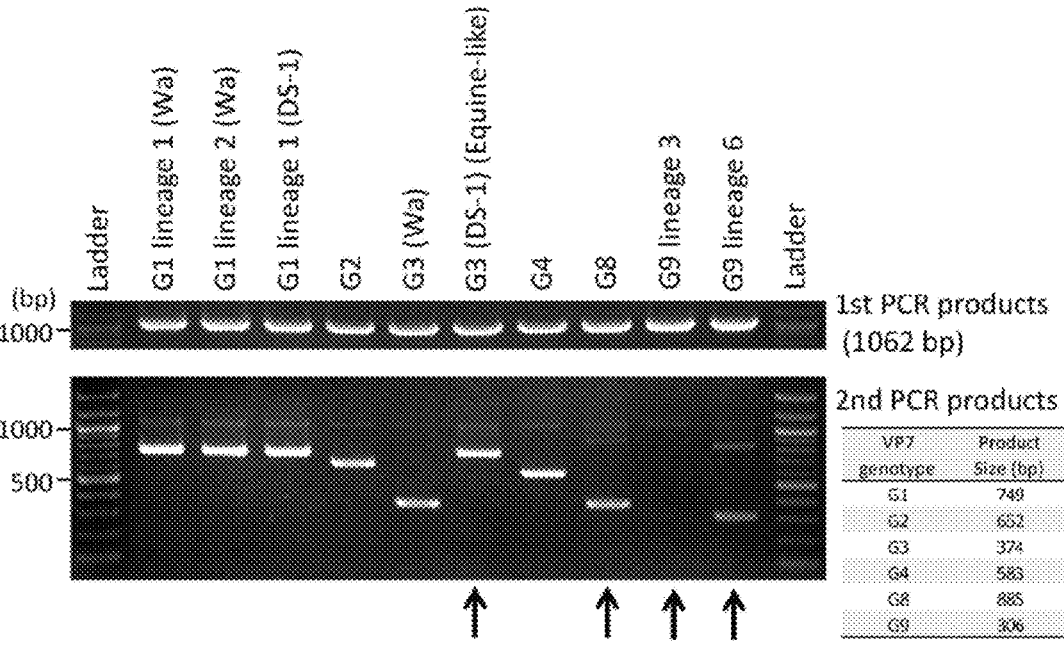
FIG. 1A illustrates an electrophoresis pattern of each genotype of rotavirus A obtained by using a primer set of Comparative example (Test system 1).

An example of an embodiment of the present invention will be described. However, it should be noted that the following example merely represents one mode of the concept of the present invention described above.

<Sense Primers (A)>

Examples of sense primers (A) include sense primers hybridizing to negative strands of the following (1) to (8). Among symbols representing bases, "R" represents guanine or adenine.

(A)(1) The sense primers hybridizing to the negative strand toward the base sequence at the positions from 802 to 834 (the positive strand number) of the double-stranded RNA or its complementary DNA of the VP7 gene segment of the G3 (the human rotavirus) type strain (AU-1) of the rotavirus A. Examples of this sense primers include sense primers including a part or the entire of the base sequence represented by CAAGG-GAAAACGTRGCAGTTA (SEQ ID NO: 3).

(A)(2) The sense primers hybridizing to the negative strand toward the base sequence at the positions from 747 to 789 (the positive strand number) of the double-stranded RNA or its complementary DNA of the VP7 gene segment of the equine-like G3 (the equine-like rotavirus) type strain (S13-30) of the rotavirus A. Examples of this sense primers include sense primers including a part or the entire of the base sequence represented by CTAGATGTTACTACGGCTAC (SEQ ID NO: 4).

(A)(3) The sense primers hybridizing to the negative strand toward the base sequence at the positions from 603 to 636 (the positive strand number) of the double-stranded RNA or its complementary DNA of the VP7 gene segment of the G9 type strain (B3458) of the rotavirus A. Examples of this sense primers include sense primers including a part or the entire of the base sequence represented by GATGGGACART-CTTGTACCATA (SEQ ID NO: 7).

(A)(4) The sense primers hybridizing to the negative strand toward the base sequence at the positions from 666 to 711 (the positive strand number) in the base sequence of the double-stranded RNA or its complementary DNA of the VP7 gene segment of the G12 type strain (Dhaka25) of the rotavirus A. Examples of this sense primers include sense primers including a part or the entire of the base sequence represented by TAC-RACAACCGACGTCACA (SEQ ID NO: 8).

(A)(5) The sense primers hybridizing to the negative strand toward the base sequence at the positions from 297 to 338 (the positive strand number) of the double-stranded RNA or its complementary DNA of the VP7 gene segment of the G1 type strain (Wa strain) of the rotavirus A. Examples of this sense primers include sense primers including a part or the entire of the base sequence represented by GTATTATCCAACT-GAAGCAAGTAC (SEQ ID NO: 1).

(A)(6) The sense primers hybridizing to the negative strand toward the base sequence at the positions from 399 to 438 (the positive strand number) of the double-stranded RNA or its complementary DNA of the VP7 gene segment of the G2 type strain (KUN) of the rotavirus A. Examples of this sense primers include sense primers including the base a part or the entire of sequence represented by TTAAAGACTACAATGAT-ATTACTACATT (SEQ ID NO: 2).

(A)(7) The sense primers hybridizing to the negative strand toward the base sequence at the positions from 468 to 507 (the positive strand number) of the double-stranded RNA or its complementary DNA of the VP7 gene segment of the G4 type strain (BrB-9) of the rotavirus A. Examples of this sense primers include sense primers including a part or the entire of the base

11 sequence represented by TTCGCTTCTGGTGAG-GAGTTG (SEQ ID NO: 5).

(A)(8) The sense primers hybridizing to the negative strand toward the base sequence at the positions from 174 to 210 (the positive strand number) of the double-stranded RNA or its complementary DNA of the VP7 gene segment of the G8 type strain (NP-130) of the rotavirus A. Examples of this sense primers include sense primers including a part or the entire of the base sequence represented by TTACRCCATTTGTAAATT-CACAG (SEQ ID NO: 6).

<Common Antisense Primers (B)>

The above common antisense primers (B) are preferably common antisense primers including a part or the entire of ACTTGCCACCATTTTTTCCA (SEQ ID NO: 9).

<Mode of Application to Nested PCR Method>

The above primer set of the present invention is used as the nested sense primers and the common nested antisense primers in the second amplification step of the nested PCR method (including the semi-nested PCR method). Then, as common outer sense primers in the first amplification step of the RT-PCR method, common outer sense primers including a part or the entire of CTCCTTTTAATGTATGGTATT-GAATATACC (SEQ ID NO: 10) can be mentioned, and, as the common outer antisense primers, common outer anti-sense primers including a part or the entire of GTATAAAANACTTGCCACCATTTTTTCCA (SEQ ID NO: 11) can be mentioned.

Note that the existing RVA detection primers, for example, the primers described in Non Patent Document 5 (specifically, the primers having base sequences of SEQ ID NO: 12 to 20 described below) can be included in the primer set of the present invention as needed, and this mode is also an embodiment of the present invention.

Examples

Example of the present invention will be described below.

[Construction of Test System 1] (1)

Preparation of Samples

In order to evaluate the multiplex PCR method, the following 11 representative strains were selected from the RVA strains of which the genotypes had been previously determined by a sequence analysis, and specimens which were known to include these RVA strains were selected and used.

Human-wt/JPN-Hokkaido/SP15-09/2015/G1 lineage 1 (Wa-like)

Human-wt/JPN-Kyoto/NT036/2013/G1 lineage 2 (Wa-like)

Human-wt/JPN-Hokkaido/SP15-06/2015/G1 lineage 1 (DS-1-like)

Human-wt/JPN-Hokkaido/To16-04/2016/G2

Human-wt/JPN-Aichi/KN105/2013/G3 (Wa-like)

Human-wt/JPN-Hokkaido/To16-01/2016/G3 (equine-like, DS-1-like)

Human-wt/JPN-Okayama/OH279/2002/G4

Human-wt/JPN-Hokkaido/TA15-07/2015/G8

Human-wt/JPN-Hokkaido/To14-25/2014/G9 lineage 3

Human-wt/JPN-Hokkaido/To16-02/2016/G9 lineage 6

Human-wt/JPN-Hokkaido/NS17-5/2017/G12

The above specimens including the RVA strains were prepared by collecting the feces from patients hospitalized for acute gastroenteritis and making 10% suspensions of the feces using PBS (10 mM, pH7.2). Viral RNAs were extracted using Direct-zol RNA Miniprep kit (Zymo Research, Irvine, CA) according to the instruction of the protocol. In summary, 80 μL of the above fecal suspension was added to 240 μL of TRIzol (registered trademark) LS reagent, and the resulting mixture was mixed using a vortex mixer. This mixture was incubated at room temperature for 5 minutes and then 320 μL of ethanol was added to the mixture. The resulting mixture was directly loaded in a spin column of the above kit. This column was subjected to centrifugal separation at 12,000×g for 1 minute, followed by washing. Purified RNAs were eluted with 40 L of DNase/RNase free water.

(2) Genotype Determination Method by Semi-Nested Multiplex PCR

The Following Gouvea Primer Set (Comparative Example):

```
1st Beg 9:
                              (SEQ ID NO: 19)
GGCTTTAAAAGAGAGAATTTCCGTCTGG

End 9:
                              (SEQ ID NO: 20)
GGTCACATCATACAATTCTAATCTAAG

2nd RVG 9:
                              (SEQ ID NO: 18)
GGTCACATCATACAATTCT aAT8 (G8):
                              (SEQ ID NO: 12)
GTCACACCATTTGTAAATTCG aBT1(G1):
                              (SEQ ID NO: 13)
CAAGTACTCAAATCAATGATGG aCT2(G2):
                              (SEQ ID NO: 14)
CAATGATATTAACACATTTTCTGTG aDT4(G4):
                              (SEQ ID NO: 15)
CGTTTCTGGTGAGGAGTTG aET3(G3):
                              (SEQ ID NO: 16)
CGTTTGAAGAAGTTGCAACAG aFT9(G9):
                              (SEQ ID NO: 17)
CTAGATGTAACTACAACTAC
```

And the Following Primer Set of Example:

```
1st VP7 C-040F:
                              (SEQ ID NO: 10)
CTCCTTTTAATGTATGGTATTGAATATACC

VP7 C-941R:
                              (SEQ ID NO: 11)
GTATAAAANACTTGCCACCATTTTTTCCA

2nd VP7 C-932R:
                              (SEQ ID NO: 9)
ACTTGCCACCATTTTTTCCA

G1-297F:
                              (SEQ ID NO: 1)
GTATTATCCAACTGAAGCAAGTAC

G2-401F:
                              (SEQ ID NO: 2)
TTAAAGACTACAATGATATTACTACATT
```

-continued

```
G3-809F:
                                    (SEQ ID NO: 3)
CAAGGGAAAACGTRGCAGTTA

G3e-757F:
                                    (SEQ ID NO: 4)
CTAGATGTTACTACGGCTAC

G4-478F:
                                    (SEQ ID NO: 5)
TTCGCTTCTGGTGAGGAGTTG

G8-179F:
                                    (SEQ ID NO: 6)
TTACRCCATTTGTAAATTCACAG

G9-606F:
                                    (SEQ ID NO: 7)
GATGGGACARTCTTGTACCATA

G12-669F:
                                    (SEQ ID NO: 8)
TACRACAACCGACGTCACA
``` were used to perform the RT-PCR (first round PCR) using the above outer primers indicated by "1st" and the multiplex PCR (second round PCR) using the nested primers indicated by "2nd". Note that "G3e" is a symbol for equine-like and indicates that the primers are related to the equine-like G3.

RT-PCR was performed with 1 μL of RNA specimens using Takara's One Step RNA PCR kit (AMV)(Takara Bio Inc., Kyoto, Japan). Prior to the reaction, RNA samples were mixed with first round primers (outer primers)(10 μmol each), and the resulting mixture was incubated at 65° C. for 5 minutes. Then, GenAmp PCR System 2700 thermal cycler (Applied Biosystems, Foster, CA, USA) was used to perform the reaction at 50° C. for 30 minutes (reverse transcription reaction) and then at 94° C. for 2 minutes, followed by 40 cycles of the amplification reaction (94° C. for 30 seconds, 50° C. for 30 seconds, and 72° C. for 90 seconds) and, finally, the extension reason at 72° C. for 5 minutes. First round PCR products thus obtained were diluted 50 times with DNase/RNase free water, and 2 μL of the diluted solutions were used for second round PCR.

The second round PCR was performed using second round primers (nested primers)(5 μmol each) and Premix Ex Taq (registered trademark) Hot Start Version (Takara Bio Inc.). Denature treatment was performed at 94° C. for 30 seconds, followed by 20 cycles of the amplification reaction (94° C. for 30 seconds, 50° C. for 30 seconds, and 72° C. for 60 seconds) and, finally, the extension reason at 72° C. for 5 minutes.

The size of PCR amplification products thus obtained was analyzed by 1.5% agarose gel electrophoresis and ethidium bromide staining. Further, as a DNAsize marker, 100 bp DNAladders (New England Biolabs, Ipswich, MA, USA) were used.

Note that, as an alternative reagent kit for the first round PCR, PrimeScript™ II High Fidelity One Step RT-PCR kit (Takara Bio Inc.) was used. In this case, the reaction was conducted under the following conditions: for the RT-PCR, the reverse transcription reaction was performed at 45° C. for 10 minutes, followed by a reaction at 98° C. for 10 seconds. Then, 40 cycles of the amplification reaction (98° C. for 10 seconds, 50° C. for 15 seconds, and 68° C. for 20 seconds) was performed and, finally, the extension reason was performed at 68° C. for 3 minutes.

The size analysis of PCR amplification products was performed in the same manner as the PCR amplification products obtained by the above basic amplification reaction system.

(3) Sequence Comparison of Viral Strains and Primers

The VP7 nucleotide sequences of the RVA type strains were obtained from GenBank and aligned using CLUSTAL W included in MEGA software package version 7.0.18 and MAFFT multiple sequence alignment software program version 7.0 (Katoh et al., 2009). Final editing was performed by Microsoft Excel 2010 software (Microsoft, Redmond, WA, USA).

[Results of Test System 1] (1)

(1) Evaluation of Gouvea Primer Set (Comparative Example)

The multiplex PCR method with the above Gouvea primer set was evaluated in the basic amplification reaction system using 10 RVA strains (G1 lineage 1 (Wa-like), G1 lineage 2 (Wa-like), G1 lineage 1 (DS-1-like), G2, G3 (Wa-like), equine-like G3 (DS-1-like), G4, G8, G9 lineage 3, and G9 lineage 6) collected in Japan.

As a result, the genotypes of Wa-like G1 lineage 1, Wa-like G1 lineage 2, DS-1-like G1, G2, Wa-like G3, and G4 could be determined without any problem. However, it was found that the following three kinds of viruses were erroneously determined or hardly determined (FIG. 1A). FIG. 1A shows the result of the basic reaction system, and, in the figure, lanes having difficulty in determination were indicated by upward arrows. First, in the equine-like G3 sample, a band with a size close to G1 (749 bp) was obtained. Further, in G8, a band was obtained at the position of G3 (374 bp). The G9 type viruses widespread in Japan are classified roughly into lineage 3 and lineage 6 by a lineage analysis. Of these, a band of lineage 3 was not detected or too weak to be determined. Further, in G9 lineage 6, a weak non-specific band was observed between G1 (749 bp) and G8 (885 bp). This result was consistent when 5 or more specimens were used.

(2) Evaluation of Primer Set of Example

Figure 1B:
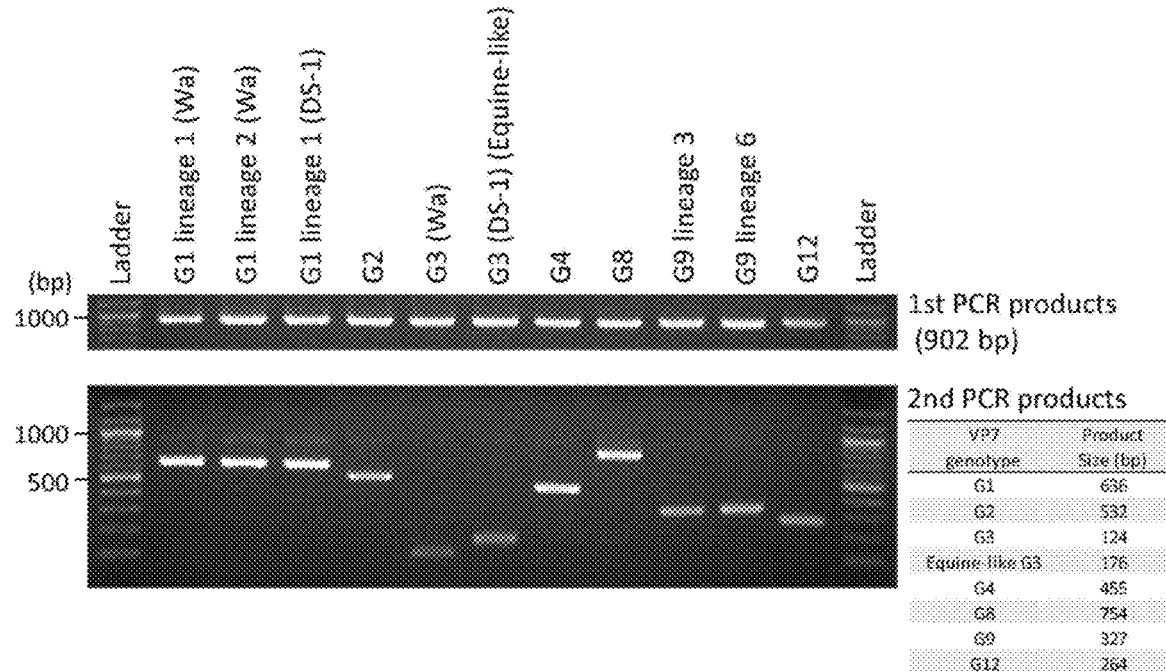
FIG. 1B illustrates an electrophoresis pattern of each genotype of rotavirus A obtained by using a primer set of Example (Test system 1).

In contrast to the above Comparative example (1), it was confirmed that, when the primer set of Example (the above; including the primer corresponding to G12) was used, the genotypes of all strains, G1, G2, human G3, equine-like G3, G4, G8, G9, as well as G12, could be accurately determined by the basic amplification reaction system (FIG. 1B). That is, bands of equine-like G3 and G1 were clearly different to each other and bands of G8 and G3 were also clearly different to each other. Further, a band of G9 lineage 3 was clearly detected. Further, the non-specific band observed in G9 lineage 6 was not observed. As described above, the parts in which detection was difficult in Comparative example were clearly detected, and, further, a band of newly added G12 was also clearly observed in a distinguishable manner. This result was consistent when 2 or more specimens were used. Further, the result was consistent whether each specimen was subjected to the above basic amplification reaction system or the amplification reaction system associated with the alternative reagent kit.

[Construction of Test System 2] (1)

Contents of Test System 2

In Test system 2, the detection performance for the genotypes of the RVA strains, in particular, human G3, equine-like G3, G9, and G12, at positions near the both ends of the gene corresponding region assigned to each strain was examined by using the semi-nested multiplex PCR as in Test system 1.

(2) Preparation of Samples

The same feces specimens used in Test system 1 were used as the specimens of G1, G2, human G3, equine-like G3, G4, G8, G9, and G12.

(3) Genotype Determination Method by Semi-Nested Multiplex PCR

The Following Primer Set:

```
1st VP7 C-040F:
                           (SEQ ID NO: 10)
CTCCTTTTAATGTATGGTATTGAATATACC

VP7 C-941R:
                           (SEQ ID NO: 11)
GTATAAAANACTTGCCACCATTTTTTCCA

2nd VP7 C-932R:
                           (SEQ ID NO: 9)
ACTTGCCACCATTTTTTCCA

G1-297F:
                           (SEQ ID NO: 1)
GTATTATCCAACTGAAGCAAGTAC

G2-401F:
                           (SEQ ID NO: 2)
TTAAAGACTACAATGATATTACTACATT

G3-beg-802F(19):
                           (SEQ ID NO: 21)
TTAGGACCAAGGGAAAACG

G3-end-812F(23):
                           (SEQ ID NO: 22)
GGGAAAACGTAGCAGTTATACAG G3e-beg-747F(21):
                           (SEQ ID NO: 23)
CAATCATAAACTAGATGTTAC G3e-end-771F(19):
                           (SEQ ID NO: 24)
GGCTACTTGTACGATCAGA

G4-478F:
                           (SEQ ID NO: 5)
TTCGCTTCTGGTGAGGAGTTG

G8-179F:
                           (SEQ ID NO: 6)
TTACRCCATTTGTAAATTCACAG

G9-beg-603F(23):
                           (SEQ ID NO: 25)
ATCGATGGGACARTCTTGTACCA G9-end-613F(24):
                           (SEQ ID NO: 26)
CAATCTTGTACCATAAAAGTGTGC G12-beg-666F(19):
                           (SEQ ID NO: 27)
ATGTACGACAACCGACGTC G12-end-689F(23):
                           (SEQ ID NO: 28)
CATTTGAAGAGGTAGCAAATGCG
``` were used to perform the RT-PCR (first round PCR) using the above outer primers indicated by "1st" and the multiplex PCR (second round PCR) using the nested primers indicated by "2nd". Note that "G3e" is a symbol for equine-like and indicates that the primers are related to the equine-like G3 same as Test system 1. RT-PCR was performed with 1 μL of RNA specimens using Takara's One Step RNA PCR kit (AMV)(Takara Bio Inc., Kyoto, Japan). Prior to the reaction, RNA samples were mixed with first round primers (outer primers)(10 μmol each), and the resulting mixture was incubated at 65° C. for 5 minutes. Then, GenAmp PCR System 2700 thermal cycler (Applied Biosystems, Foster, CA, USA) was used to perform the reaction at 50° C. for 30 minutes (reverse transcription reaction) and then at 94° C. for 2 minutes, followed by 40 cycles of the amplification reaction (94° C. for 30 seconds, 50° C. for 30 seconds, and 72° C. for 90 seconds) and, finally, the extension reason at 72° C. for 5 minutes. First round PCR products thus obtained were diluted 50 times with DNase/RNase free water, and 2 μL of the diluted solutions were used for second round PCR.

The second round PCR was performed using second round primers (nested primers)(5 μmol each) and Premix Ex Taq (registered trademark) Hot Start Version (Takara Bio Inc.). Denature treatment was performed at 94° C. for 30 seconds, followed by 20 cycles of the amplification reaction (94° C. for 30 seconds, 50° C. for 30 seconds, and 72° C. for 60 seconds) and, finally, the extension reason at 72° C. for 5 minutes.

The size of PCR amplification products thus obtained was analyzed by 1.5% agarose gel electrophoresis and ethidium bromide staining. Further, as a DNA size marker, 100 bp DNAladders (New England Biolabs, Ipswich, MA, USA) were used.

Note that, as an alternative reagent kit for the first round PCR, PrimeScript™ II High Fidelity One Step RT-PCR kit (Takara Bio Inc.) was used. In this case, the reaction was conducted under the following conditions: for the RT-PCR, the reverse transcription reaction was performed at 45° C. for 10 minutes, followed by a reaction at 98° C. for 10 seconds. Then, 40 cycles of the amplification reaction (98° C. for 10 seconds, 50° C. for 15 seconds, and 68° C. for 20 seconds) was performed and, finally, the extension reason was performed at 68° C. for 3 minutes.

The size analysis of PCR amplification products was performed in the same manner as the PCR amplification products obtained by the above basic amplification reaction system.

(4) Sequence Comparison of Viral Strains and Primers

The VP7 nucleotide sequences of the RVA type strains were obtained from GenBank and aligned using CLUSTAL W included in MEGA software package version 7.0.18 and MAFFT multiple sequence alignment software program version 7.0 (Katoh et al., 2009). Final editing was performed by Microsoft Excel 2010 software (Microsoft, Redmond, WA, USA).

[Results of Test System 2]

Figure 2:
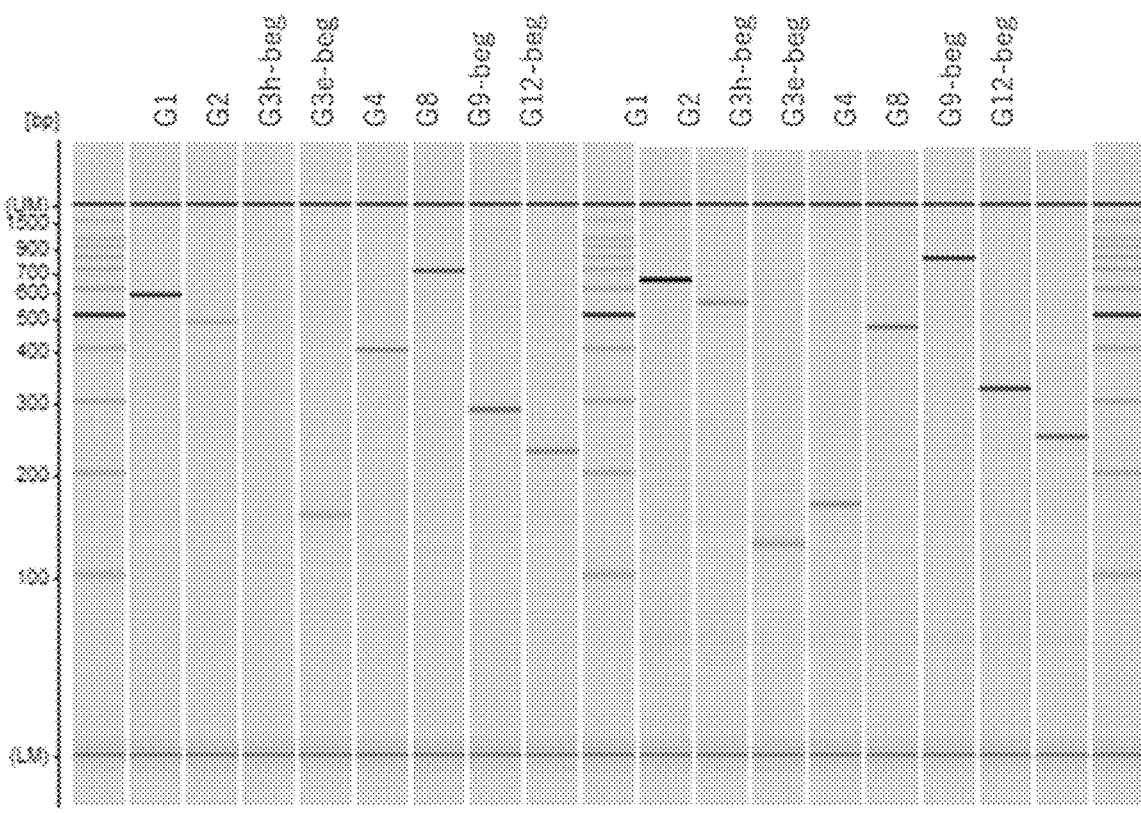
FIG. 2 illustrates an electrophoresis pattern of each genotype of rotavirus A obtained by using a primer set of Example (Test system 2).

The primers corresponding to the both ends of the gene regions of the type strains of human G3, equine-like G3, G9, and G12, constituting more basic elements, in the detection method of the present invention, that is, G3-beg-802F (5' side: corresponding to G3 h-beg in FIG. 2) and G3-end-812F (5' side: corresponding to G3 h-end in FIG. 2) for human G3; G3e-beg-747F (5' side: corresponding to G3e-beg in FIG. 2) and G3e-end-771F (5' side: corresponding to G3e-end in FIG. 2) for equine-like G3; G9-beg-603F (5' side: corresponding to G9-beg in FIG. 2) and G9-end-613F (5' side: corresponding to G9-end in FIG. 2) for G9; and G12-beg-666F (5' side: corresponding to G12-beg in FIG. 2) and G12-end-689F (5' side: corresponding to G12-end in FIG. 2) for G12; as well as the addable primers corresponding to the type strains of G1, G2, G4, and G8 in the present invention, were used to perform the multiplex PCR. As a result, by using the primer pair of the both ends of the gene region corresponding to each of the basic type strains, a clear band surely distinguishable from others could be observed despite a difference in band intensities. Thus, it was shown that detection method of the present invention could be performed in the entire gene region defined in each of the type strains in the present invention. Further, from this result, it is speculated that the addable primers can be similarly applied to the defined entire gene regions in the detection method of the present invention.

INDUSTRIAL APPLICABILITY

Determining quickly and accurately the genotypes (G types) of the VP7 gene segment of rotavirus A (RVA) is industrially important from the following viewpoints.

(1) The rotavirus VP7 protein is the most important viral protein for biological defense. That is, the VP7 protein that constitutes the outermost part of the rotavirus particle is relatively easily recognized by the living body among rotavirus proteins. Upon rotavirus infection, antibodies against the VP7 protein are preferentially produced. On the other hand, to the different genotypes of VP7, the previously produced antibodies become ineffective or less effective. Thus, grasping the epidemic state of VP7 of the rotavirus in a genotype unit level provides a key to estimate the human immune state in the rotavirus epidemic region and is also important to predict future epidemics and evaluate effects of vaccine.

(2) The rotavirus genome is constituted by 11 gene segments and many types are found in each gene. Thus, it is simply speculated that the number of combinations of the genotypes becomes enormous. However, in reality, the genotype constitution patterns in each rotavirus strain are generally limited, and thus determining the genotypes (G types) of the VP7 gene segment generally makes it possible to predict other genotype. Thus, in a normal clinical examination site, there is less necessity to determine the genotypes of other gene segments in addition to the VP7 genotypes of the rotavirus.

(3) As the rotaviruses capable of infecting human other than RVA, rotavirus B (RVB) and rotavirus C (RVC) can be mentioned at present. However, not only because the detection frequency of RVA is significantly high, but also because types of the epidemic strains of RVB and RVC are limited, there is less necessity to take the trouble to determine the genotypes of RVB and RVC. Thus, determining only the genotypes (G types) of the VP7 gene segments of RVA will do for grasping the ongoing state of the rotavirus in a normal clinical examination site.

As described in the above (1) to (3), determining the genotypes (G types) of the VP7 gene segments of RVA is an essential work against the rotavirus, and the present invention allowing this work to be performed quickly and accurately is considered industrially very important.

---

The invention claimed is:

1. A method for diagnosing a genotype of a rotavirus infecting a patient comprising:

obtaining a gene from a specimen;

amplifying the gene by applying a PCR method to the gene obtained from the specimen to obtain a gene amplification product; and determining the genotype of the rotavirus infecting the patient from the gene amplification product;

wherein the amplifying step comprises hybridizing the gene to sense primers (A) and common antisense primers (B), wherein the sense primers (A) are selected from one or more of the following (A)(1) to (A)(4):

(A)(1) sense primers including the entire sequence of SEQ ID NO: 3;

(A)(2) sense primers including the entire sequence of SEQ ID NO: 4;

(A)(3) sense primers including the entire sequence of SEQ ID NO: 7; and (A)(4) sense primers including the entire sequence of SEQ ID NO: 8, and wherein the common antisense primers (B) include the entire sequence of SEQ ID NO: 9.

2. The method according to claim 1, wherein sense primers (A) further includes one to four kinds selected from the following (A)(5) to (A)(8):

(A)(5) sense primers including the entire sequence of SEQ ID NO: 1;

(A)(6) sense primers including the entire sequence of SEQ ID NO: 2;

(A)(7) sense primers including the entire sequence of SEQ ID NO: 5; and (A)(8) sense primers including the entire sequence of SEQ ID NO: 6.

3. The method according to claim 1, wherein the gene is in the form of an RNA, wherein between the obtaining step and the amplifying step, an RT-PCR step is used to obtain a template for the amplifying step, wherein the amplifying step is a second amplification step in a nested-PCR method wherein, the RT-PCR step comprises hybridizing the RNA with common outer sense primers (O)(1) including the entire sequence of SEQ ID NO: 10, and with common outer sense primers (O)(2) including the entire sequence of SEQ ID NO: 11.

\* \* \* \* \*

SEQUENCE LISTING

<160> NUMBER OF SEQ ID NOS: 28

<210> SEQ ID NO 1
<211> LENGTH: 24
<212> TYPE: DNA
<213> ORGANISM: Artificial Sequence
<220> FEATURE:
<223> OTHER INFORMATION: Chemically-synthesized primer

<400> SEQUENCE: 1
gtattatcca actgaagcaa gtac                                    24

<210> SEQ ID NO 2
<211> LENGTH: 28
<212> TYPE: DNA
<213> ORGANISM: Artificial Sequence
<220> FEATURE:
<223> OTHER INFORMATION: Chemically-synthesized primer

<400> SEQUENCE: 2
ttaaagacta caatgatatt actacatt                               28

<210> SEQ ID NO 3
<211> LENGTH: 21
<212> TYPE: DNA
<213> ORGANISM: Artificial Sequence
<220> FEATURE:
<223> OTHER INFORMATION: Chemically-synthesized primer

<400> SEQUENCE: 3
caagggaaaa cgtrgcagtt a                                       21

<210> SEQ ID NO 4
<211> LENGTH: 20

-continued

```
<212> TYPE: DNA
<213> ORGANISM: Artificial Sequence
<220> FEATURE:
<223> OTHER INFORMATION: Chemically-synthesized primer

<400> SEQUENCE: 4
ctagatgtta ctacggctac                                              20

<210> SEQ ID NO 5
<211> LENGTH: 21
<212> TYPE: DNA
<213> ORGANISM: Artificial Sequence
<220> FEATURE:
<223> OTHER INFORMATION: Chemically-synthesized primer

<400> SEQUENCE: 5
ttcgcttctg gtgaggagtt g                                            21

<210> SEQ ID NO 6
<211> LENGTH: 23
<212> TYPE: DNA
<213> ORGANISM: Artificial Sequence
<220> FEATURE:
<223> OTHER INFORMATION: Chemically-synthesized primer

<400> SEQUENCE: 6
ttacrccatt tgtaaattca cag                                          23

<210> SEQ ID NO 7
<211> LENGTH: 22
<212> TYPE: DNA
<213> ORGANISM: Artificial Sequence
<220> FEATURE:
<223> OTHER INFORMATION: Chemically-synthesized primer

<400> SEQUENCE: 7
gatgggacar tcttgtacca ta                                           22

<210> SEQ ID NO 8
<211> LENGTH: 19
<212> TYPE: DNA
<213> ORGANISM: Artificial Sequence
<220> FEATURE:
<223> OTHER INFORMATION: Chemically-synthesized primer

<400> SEQUENCE: 8
tacracaacc gacgtcaca                                               19

<210> SEQ ID NO 9
<211> LENGTH: 20
<212> TYPE: DNA
<213> ORGANISM: Artificial Sequence
<220> FEATURE:
<223> OTHER INFORMATION: Chemically-synthesized primer

<400> SEQUENCE: 9
acttgccacc atttttttcca                                             20

<210> SEQ ID NO 10
<211> LENGTH: 30
<212> TYPE: DNA
<213> ORGANISM: Artificial Sequence
<220> FEATURE:
<223> OTHER INFORMATION: Chemically-synthesized primer

<400> SEQUENCE: 10
```
ctccttttaa tgtatggtat tgaatatacc                                        30

<210> SEQ ID NO 11
<211> LENGTH: 29
<212> TYPE: DNA
<213> ORGANISM: Artificial Sequence
<220> FEATURE:
<223> OTHER INFORMATION: Chemically-synthesized primer
<220> FEATURE:
<221> NAME/KEY: misc_feature
<222> LOCATION: (9)..(9)
<223> OTHER INFORMATION: n is a, c, g, or t

<400> SEQUENCE: 11
gtataaaana cttgccacca tttttttcca                                        29

<210> SEQ ID NO 12
<211> LENGTH: 21
<212> TYPE: DNA
<213> ORGANISM: Artificial Sequence
<220> FEATURE:
<223> OTHER INFORMATION: Chemically-synthesized primer

<400> SEQUENCE: 12
gtcacaccat ttgtaaattc g                                                 21

<210> SEQ ID NO 13
<211> LENGTH: 22
<212> TYPE: DNA
<213> ORGANISM: Artificial Sequence
<220> FEATURE:
<223> OTHER INFORMATION: Chemically-synthesized primer

<400> SEQUENCE: 13
caagtactca aatcaatgat gg                                                22

<210> SEQ ID NO 14
<211> LENGTH: 25
<212> TYPE: DNA
<213> ORGANISM: Artificial Sequence
<220> FEATURE:
<223> OTHER INFORMATION: Chemically-synthesized primer

<400> SEQUENCE: 14
caatgatatt aacacatttt ctgtg                                             25

<210> SEQ ID NO 15
<211> LENGTH: 19
<212> TYPE: DNA
<213> ORGANISM: Artificial Sequence
<220> FEATURE:
<223> OTHER INFORMATION: Chemically-synthesized primer

<400> SEQUENCE: 15
cgtttctggt gaggagttg                                                    19

<210> SEQ ID NO 16
<211> LENGTH: 21
<212> TYPE: DNA
<213> ORGANISM: Artificial Sequence
<220> FEATURE:
<223> OTHER INFORMATION: Chemically-synthesized primer

<400> SEQUENCE: 16
cgtttgaaga agttgcaaca g                                                 21

-continued

```
<210> SEQ ID NO 17
<211> LENGTH: 20
<212> TYPE: DNA
<213> ORGANISM: Artificial Sequence
<220> FEATURE:
<223> OTHER INFORMATION: Chemically-synthesized primer

<400> SEQUENCE: 17
ctagatgtaa ctacaactac                                              20

<210> SEQ ID NO 18
<211> LENGTH: 19
<212> TYPE: DNA
<213> ORGANISM: Artificial Sequence
<220> FEATURE:
<223> OTHER INFORMATION: Chemically-synthesized primer

<400> SEQUENCE: 18
ggtcacatca tacaattct                                               19

<210> SEQ ID NO 19
<211> LENGTH: 28
<212> TYPE: DNA
<213> ORGANISM: Artificial Sequence
<220> FEATURE:
<223> OTHER INFORMATION: Chemically-synthesized primer

<400> SEQUENCE: 19
ggctttaaaa gagagaattt ccgtctgg                                     28

<210> SEQ ID NO 20
<211> LENGTH: 27
<212> TYPE: DNA
<213> ORGANISM: Artificial Sequence
<220> FEATURE:
<223> OTHER INFORMATION: Chemically-synthesized primer

<400> SEQUENCE: 20
ggtcacatca tacaattcta atctaag                                      27

<210> SEQ ID NO 21
<211> LENGTH: 19
<212> TYPE: DNA
<213> ORGANISM: Artificial Sequence
<220> FEATURE:
<223> OTHER INFORMATION: Chemically-synthesized primer

<400> SEQUENCE: 21
ttaggaccaa gggaaaacg                                               19

<210> SEQ ID NO 22
<211> LENGTH: 23
<212> TYPE: DNA
<213> ORGANISM: Artificial Sequence
<220> FEATURE:
<223> OTHER INFORMATION: Chemically-synthesized primer

<400> SEQUENCE: 22
gggaaaacgt agcagttata cag                                          23

<210> SEQ ID NO 23
<211> LENGTH: 21
<212> TYPE: DNA
<213> ORGANISM: Artificial Sequence
<220> FEATURE:
<223> OTHER INFORMATION: Chemically-synthesized primer
```

-continued

```
<400> SEQUENCE: 23
caatcataaa ctagatgtta c                                                    21

<210> SEQ ID NO 24
<211> LENGTH: 19
<212> TYPE: DNA
<213> ORGANISM: Artificial Sequence
<220> FEATURE:
<223> OTHER INFORMATION: Chemically-synthesized primer

<400> SEQUENCE: 24
ggctacttgt acgatcaga                                                       19

<210> SEQ ID NO 25
<211> LENGTH: 23
<212> TYPE: DNA
<213> ORGANISM: Artificial Sequence
<220> FEATURE:
<223> OTHER INFORMATION: Chemically-synthesized primer

<400> SEQUENCE: 25
atcgatggga cartcttgta cca                                                  23

<210> SEQ ID NO 26
<211> LENGTH: 24
<212> TYPE: DNA
<213> ORGANISM: Artificial Sequence
<220> FEATURE:
<223> OTHER INFORMATION: Chemically-synthesized primer

<400> SEQUENCE: 26
caatcttgta ccataaaagt gtgc                                                 24

<210> SEQ ID NO 27
<211> LENGTH: 19
<212> TYPE: DNA
<213> ORGANISM: Artificial Sequence
<220> FEATURE:
<223> OTHER INFORMATION: Chemically-synthesized primer

<400> SEQUENCE: 27
atgtacgaca accgacgtc                                                       19

<210> SEQ ID NO 28
<211> LENGTH: 23
<212> TYPE: DNA
<213> ORGANISM: Artificial Sequence
<220> FEATURE:
<223> OTHER INFORMATION: Chemically-synthesized primer

<400> SEQUENCE: 28
catttgaaga ggtagcaaat gcg                                                  23
```